United States Patent
Chen et al.

(10) Patent No.: US 9,404,163 B2
(45) Date of Patent: Aug. 2, 2016

(54) PSEUDOMONAS PUTIDA STRAIN AS WELL AS ITS MICROBIAL INOCULUM AND APPLICATION

(71) Applicant: ZHEJIANG UNIVERSITY OF TECHNOLOGY, Hangzhou, Zhejiang Province (CN)

(72) Inventors: Jianmeng Chen, Hangzhou (CN); Dongzhi Chen, Hangzhou (CN); Jiexu Ye, Hangzhou (CN); Limei Han, Hangzhou (CN); Yiming Sun, Hangzhou (CN)

(73) Assignee: ZHEJIANG UNIVERSITY OF TECHNOLGY, Hangzhou, Zhejiang Province (CN)

( * ) Notice: Subject to any disclaimer, the term of this patent is extended or adjusted under 35 U.S.C. 154(b) by 0 days.

(21) Appl. No.: 14/591,740

(22) Filed: Jan. 7, 2015

(65) Prior Publication Data

US 2016/0083807 A1    Mar. 24, 2016

(30) Foreign Application Priority Data

Sep. 18, 2014   (CN) .......................... 2014 1 0479144

(51) Int. Cl.
  *C12R 1/40*      (2006.01)
  *B01D 53/84*   (2006.01)
  *C12N 1/20*     (2006.01)

(52) U.S. Cl.
  CPC . *C12R 1/40* (2013.01); *B01D 53/84* (2013.01); *C12N 1/20* (2013.01)

(58) Field of Classification Search
  CPC ............. C12N 1/20; C12R 1/40; B01D 53/84
  See application file for complete search history.

(56) References Cited

FOREIGN PATENT DOCUMENTS

CN           103667119 A   *   3/2014   ............... C12N 1/20

OTHER PUBLICATIONS

Jiang et al. "Nitric oxide removal from flue gas with a biotrickling filter using Pseudomonas putida" Journal of Hazardous Materials 164(2009) 432-441.*

* cited by examiner

*Primary Examiner* — Louise W Humphrey
*Assistant Examiner* — Stephen A Perkins
(74) *Attorney, Agent, or Firm* — Jiwen Chen

(57) ABSTRACT

A *Pseudomonas putida* strain is named as *Pseudomonas putida* S-1, which was preserved at China Center for Type Culture Collection (CCTCC) on Sep. 25, 2013 with the deposit number of CCTCC NO: M2013444. The strain of this invention takes isopropanol, ethanal, dipropyl disulfide, diethyl disulfide and propanethiol as the sole carbon source for effective degradation of substrate simultaneously with the energy growth. Furthermore, it can obtain a perfect growth in different cultivation modes owing to high substrate tolerance, which has laid down a solid foundation for engineering application for elimination of volatile organic compounds contained exhaust gas by means of biological purification.

16 Claims, 8 Drawing Sheets

SEQUENCE LISTING

<160> NUMBER OF SEQ ID NOS: 3

<210> SEQ ID NO 1
<211> LENGTH: 1436
<212> TYPE: DNA
<213> ORGANISM: Pseudomonas putida

<400> SEQUENCE: 1

```
tgcagtcgag cggatgagaa gagcttgctc ttcgattcag cggcggacgg gtgagtaata      60
cctaggaatc tgcctggtag tgggggacaa cgtttcgaaa ggaacgctaa taccgcatac     120
gtcctacggg agaaagcagg ggaccttcgg gccttgcgct atcagatgag cctaggtcgg     180
attagctagt tggtgaggta atggctcacc aaggctacga tccgtaactg gtctgagagg     240
atgatcagtc acactggaac tgagacacgg tccagactcc tacgggaggc agcagtgggg     300
aatattggac aatgggcgaa agcctgatcc agccatgccg cgtgtgtgaa gaaggtcttc     360
ggattgtaaa gcactttaag ttgggaggaa gggcagtaag cgaataccgt gctgttttga     420
cgttaccgac agaataagca ccggctaact ctgtgccagc agccgcggta atacagaggg     480
tgcaagcgtt aatcggaatt actgggcgta aagcgcgcgt aggtggttcg ttaagttgga     540
tgtgaaatcc ccgggctcaa cctgggaact gcatccaaaa ctggcgagct agagtagggc     600
agagggtggt ggaatttcct gtgtagcggt gaaatgcgta gatataggaa ggaacaccag     660
tggcgaaggc gaccacctgg gctcatactg acactgaggt gcgaaagcgt ggggagcaaa     720
caggattaga taccctggta gtccacgccg taaacgatgt caactagccg ttggaatcct     780
tgagatttta gtggcgcagc taacgcatta agttgaccgc ctggggagta cggccgcaag     840
gttaaaactc aaatgaattg acgggggccc gcacaagcgg tggagcatgt ggtttaattc     900
gaagcaacgc gaagaacctt accaggcctt gacatccaat gaactttcca gagatggatt     960
ggtgccttcg ggaacattga cacaggtgct gcatggctgt cgtcagctcg tgtcgtgaga    1020
tgttgggtta agtcccgtaa cgagcgcaac ccttgtcctt agttaccagc acgttatggt    1080
gggcactcta aggagactgc cggtgacaaa ccggaggaag gtgggatgac gtcaagtca     1140
tcatggccct tacggcctgg gctacacacg tgctacaatg gtcggtacag agggtcgcca    1200
agccgcgagg tggagctaat ctcacaaaac cgatcgtagt ccggatcgca gtctgcaact    1260
cgactgcgtg aagtcggaat cgctagtaat cgcgaatcag aatgtcgcgg tgaatacgtt    1320
cccgggcctt gtacacaccg cccgtcacac catgggagtg ggttgcacca gaagtagcta    1380
gtctaacctt cgggaggacg gttaccacgg tgtgattcat gactggggtg aagtcg        1436
```

<210> SEQ ID NO 2
<211> LENGTH: 20
<212> TYPE: DNA
<213> ORGANISM: Artificial Sequence
<220> FEATURE:
<223> OTHER INFORMATION: SYNTHESIZED

<400> SEQUENCE: 2

```
agagtttgat cctggctcag                                                   20
```

<210> SEQ ID NO 3
<211> LENGTH: 20
<212> TYPE: DNA
<213> ORGANISM: Artificial Sequence
<220> FEATURE:
<223> OTHER INFORMATION: SYNTHESIZED

```
<400> SEQUENCE: 3
agaaaggagg tgatccagcc                                                20
```

PSEUDOMONAS PUTIDA STRAIN AS WELL AS ITS MICROBIAL INOCULUM AND APPLICATION

The present application claims the priority of Chinese Patent Application No. 201410479144.X, filed Sep. 18, 2014, which is hereby incorporated by reference.

FIELD OF THE INVENTION

The present invention is related to the technical field of microorganisms, particularly related to a kind of *pseudomonas putida* strain as well as its microbial inoculums and application.

BACKGROUND OF THE INVENTION

Volatile organic compounds (VOCs) are a kind of air pollutant similarly dangerous to particulate matters. As indicated in relevant studies, VOCs with a concentration of up to 0.2-0.3 mg/m$^3$ may result in such discomfort symptoms as irritation to human body; whereas VOCs with a concentration up to 3-25 mg/m$^3$ may result in such symptoms as irritation and headache; VOCs with a concentration over 25 mg/m$^3$ may result in extremely obvious toxic effect to the human body. Furthermore, VOCs may also incur such secondary pollution as photo-chemical smog in addition to its inherent hazards.

Most of the industrial exhaust gases containing VOCs are from industries that take coal, petroleum and natural gas as the sources for organic compounds or relevant chemical industries; wherein, alcohols and aldehyde are extensively used as industrial solvents, thus generating large amounts of discharge. In view of the present status of industrial VOCs exhaust gases of low concentration and large quantity, biological purification technology is a relatively ideal treatment approach. However, for such VOCs as isopropanol and ethanal, the effect of biological treatment is unsatisfactory. In recent years, researchers have tried to solve the problem of decomposition of VOCs by selecting microorganisms with high efficiency.

*Bacillus pallidus* ST3, an isopropanol degrading bacteria as selected by Bustard and his colleagues, is available for degrading 24 g/L isopropanol under the temperature of 60° C. McEvoy and his colleagues discovered *Chlorella vulgaris* which is effective for degrading of isopropanol of high concentration with specific growth rate for degrading 2-16 g/L isopropanol up to 0.0017-0.0038 h$^{-1}$. Mohammad and his colleagues have successfully separated *Sphingobacterium mizutae* ST2, a strain for degrading isopropanol with maximum specific growth rate and maximum specific degrading rate (concentration of isopropanol is 7.5 g/L) up to 0.0045 h$^{-1}$ and 0.045 gram/(gram×hour) respectively.

In addition to such VOCs as alcohols and aldehyde, effluvial organic sulfides, such as sulfoether and mercaptan compounds, have higher requirements for pollution control due to low olfactory coefficient. With regard to demethyl sulphide and dimethyl disulphide, degrading bacteria reported includes *Hyphomicrobia* sp. EG, *Thiobacilli* sp. ASN-1, *Pseudomonas acidovorans* and Methanogens sp. MPT4; wherein, specific growth rate of *Thiobacillus* sp. ASN-1, *Hyphomicrobium* sp. EG and *Methanosarcina* MPT4 is up to 0.10 h$^{-1}$, a0.08 h$^{-1}$ and 0.01 h$^{-1}$ respectively.

Chinese Patent Publication No. CN 103667119 A has disclosed a strain for degrading ethyl mercaptan as well as its culture method and application. Such strain is named as *Pseudomonas* sp. WL2 preserved at China General Microbiological Culture Collection Center (CGMCC) on Jul. 8, 2013 with the deposit number of CGMCC NO. 7898. Such strain belongs to aerobic gram-negative bacteria, which can grow by taking ethyl mercaptan as the sole carbon source and energy and thoroughly transform them into $CO_2$ and $H_2O$ through mineralization. Under pure culture conditions, such strain is capable of degrading ethyl mercaptan at the temperature of 25~30° C. and pH value of 6~8. Such strain features in excellent substrate accommodation and universality, which can also be used for degrading propanethiol and methanol; however, its substrate tolerance and universality are not so satisfactory.

SUMMARY OF THE INVENTION

The present invention provides a *Pseudomonas putida* of high substrate tolerance for degrading such volatile organic compounds as isopropanol, aldehyde, dipropyl disulfide, diethyl disulfide and propanethiol.

The *pseudomonas putida* strain named as *pseudomonas putida* S-1 was preserved at China Center for Type Culture Collection (CCTCC) of Wuhan University on Sep. 25, 2013 with the deposit number of CCTCC NO: M2013444.

The cell of such strain is rod-shaped with size up to (0.4-0.7)μm×(1.4-1.7)μm, with flagella but no gemmae; the small round bacteria colony is white with plump profile, smooth, wet and easy to be picked; the lawn grows along the streak, aerobic, with positive oxydase reaction; positive arginine hydrolase and catalase, and negative in indole reaction, Methyl Red reaction, Voges-Proskauer reaction and gram staining.

16S rRNA of the *pseudomonas putida* strain is shown in SEQ ID NO.1.

The *pseudomonas putida* S-1 is available for different culture modes, including shake-flask culture, liquid fermentation (stirred fermentation and airlift fermentation), semi-solid fermentation and solid fermentation.

The present invention also provides a microbial inoculum containing the *Pseudomonas putida* S-1.

The inoculum is available in solid, semi-solid or liquid form; solid and semi-solid inoculums are preferred.

The solid microbial inoculum can be obtained by mixing the liquid bacteria and the solid carrier; solid carrier contains 60-70% activated carbon powder, 15-25% sawdust, 10-20% dry soil and 5% diatomaceous earth; The solid microbial inoculum can also be obtained from the culture medium composed of 30-40% turf, 30-40% wheat bran, 5-10% beef extract, 5-10% peptone and 5-10% inorganic salt through solid fermentation.

The semi-solid microbial inoculum can be obtained from semi-solid culture medium through semi-solid fermentation; the semi-solid culture medium takes agar as the solid.

The present invention also provides application of *Pseudomonas putida* S-1 and microbial inoculums containing *Pseudomonas putida* S-1 in degrading volatile organisms.

The volatile organic compound is one or more of isopropanol, ethanal, dipropyl disulfide, diethyl disulfide and propanethiol.

The present invention also provides a treatment method containing VOCs exhaust gas, comprising the following steps:

(1) transplanting the *Pseudomonas putida* S-1 or the microbial inoculums containing such strain to the bioreactor;

(2) passing the VOC-contained exhaust gas through the bioreactor.

In a preferred embodiment, the reaction conditions for the bioreactor are stated as follows: pH value, temperature and salinity is 6.0~8.0, 25° C.~30° C. and 0°~1.5% respectively.

The bioreactor belongs to stirred bioreactor, airlift bioreactor or biotrickling filter.

The strain of the present invention is available for effective degradation of substrates while growing by taking isopropanol, ethanal, dipropyl disulfide, diethyl disulfide and propanethiol as the sole carbon source and energy. Furthermore, it can obtain an excellent growth in different cultivation modes with high substrate tolerance, which has laid down a solid foundation for engineering application for elimination of VOCs-contained exhaust gas by means of biological purification.

BRIEF DESCRIPTION OF THE DRAWINGS

FIG. 2A, FIG. 2B, FIG. 2C, FIG. 2D and FIG. 2E refer to isopropanol, ethanal, dipropyl disulfide, diethyl disulfide and propanethiol, respectively.

FIG. 3A, FIG. 3B, FIG. 3C and FIG. 3D refer to preliminary culture in eutrophia culture medium, inorganic salt (propanethiol contained), citric acid culture medium and inorganic salt culture medium (yeast powder contained), respectively.

FIG. 4A, FIG. 4B and FIG. 4C refer to pH, temperature and salinity, respectively.

PREFERRED EMBODIMENTS

Embodiment 1

Separation and Purification of Strain

Activated sludge was collected on spot from the sewage tank of one pharmaceutical factory in Zhejiang Province, for acclimatization and enrichment by taking such VOCs as isopropanol, ethanal, dipropyl disulfide, diethyl disulfide and propanethiol as the carbon source and energy. Several months later, activated sludge was transplanted to the 250 ml sealed saline bottle containing 50 mL inorganic salt culture medium for continuous culture and enrichment by taking such VOCs as isopropanol, ethanal, dipropyl disulfide, diethyl disulfide and propanethiol as the sole carbon source and energy. Tests were conducted under the constant temperature (30±1° C.) and aerobic conditions.

Solid culture medium was used to dilute and coat the bacteria solution gathered from numerous and successive enrichment in the saline bottle, and a single colony was selected according to discrepancy of the bacteria colonies. The single colony was transferred through numerous streaked separations to an inorganic culture medium that took isopropanol, ethanal, dipropyl disulfide, diethyl disulfide and propanethiol as the sole carbon source and energy, and test its degrading activity was tested. A strain with high degrading capability was selected for further separation and purification to obtain the strain with degrading activity.

The 1 L inorganic salt culture medium comprises: 0.5-4.5 g Na2HPO4.12H2O, 0.5-4 g KH2PO4, 0.2-2 g NH4Cl, 0.01-0.023 g $CaCl_2$, 0.05-0.3 g $MgCl_2$, 1 mL mother liquid of trace elements; water with pH value of 7.0 is used as solvent. The concentrations of the mother liquid of trace elements: 0.5-2.0 g/L $FeCl_2.7H_2O$, 0.01-0.02 g/L $CuCl_2.5H_2O$, 0.01-0.03 g/L $H_3BO_3$, 0.05-0.15 g/L $MnCl_2.4H2O$, 0.1-0.3 g/L $ZnCl_2.7H_2O$, 0.01-0.03 g/L $Na_2MnO_4.2H_2O$ and 0.01-0.02 g/L $CoCl_2.6H_2O$; water is used as solvent for high-pressure sterilization for 40 min under the temperature of 110° C.

The solid inorganic salt culture medium was prepared by adding 1.5%-1.8% agar into a liquefied inorganic salt culture medium for high-pressure sterilization for 40 min under the temperature of 110° C.

The solid culture medium comprises: 0.10-0.50 g/L yeast extract, 0.10-0.50 g/L peptone, 0.10-0.50 g/L casein, 0.10-0.50 g/L glucose, 0.10-0.50 g/L soluble starch, 0.10-0.30 g/L sodium pyruvate, 0.10-0.30 g/L $KH_2PO_4$, 0.01-0.05 g/L $MgSO_4.7H_2O$ and 12.0-18.0 g/L agar. The crystallized $KH_2PO_4$ or $KH_2PO_4$ was used to adjust the final pH value to 7.2 before addition of agar. After the agar was added, the culture medium was heated to boil and the agar was sterilized for 20 min under high-pressure of 121° C. after it was dissolved.

Embodiment 2

Strain Verification

Figure 1:
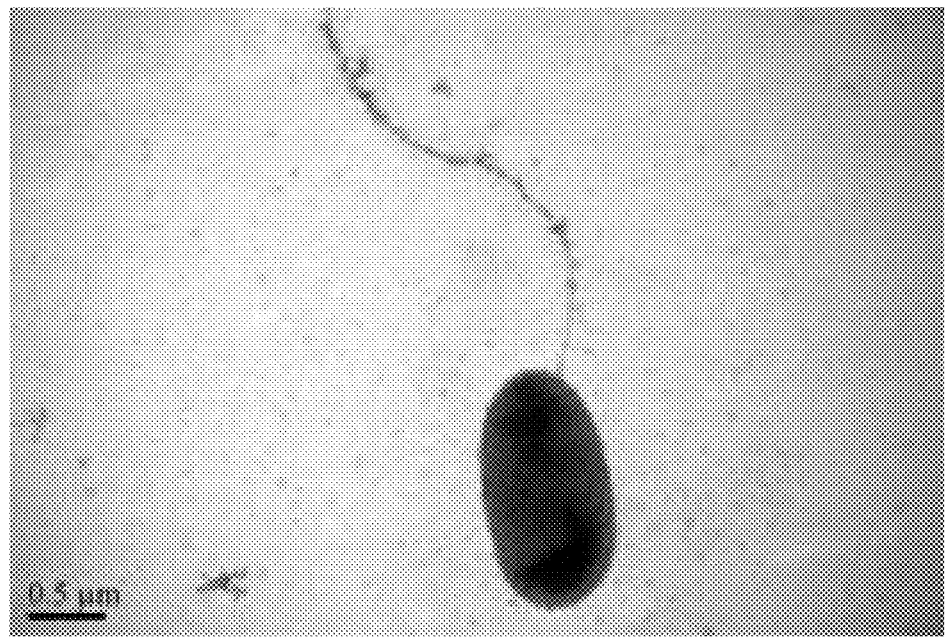
FIG. 1 is the picture of transmission electron microscope for *Pseudomonas putida* S-1.
Figure 2A:
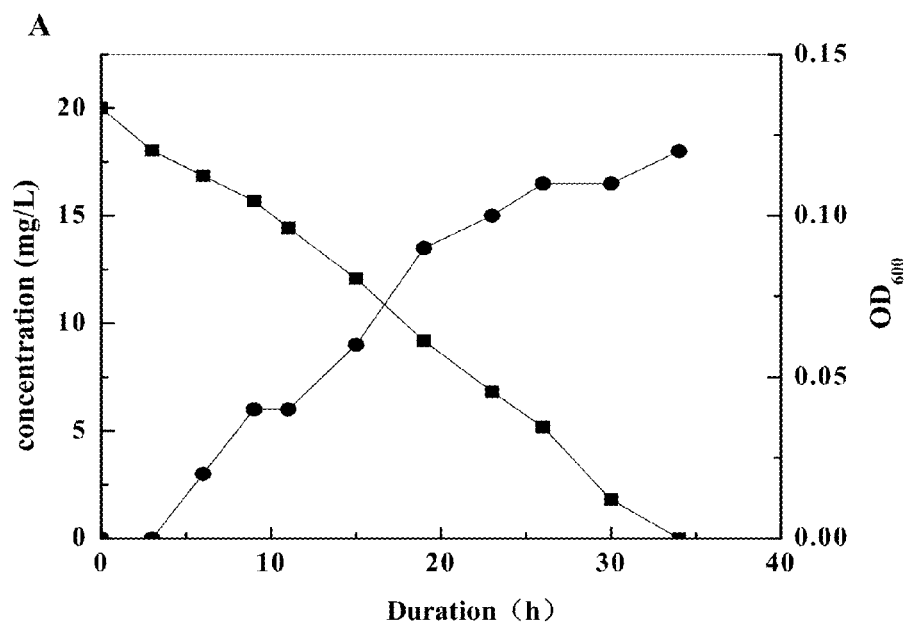
FIG. 2A, FIG. 2B, FIG. 2C, FIG. 2D and FIG. 2E show how *pseudomonas putida* S-1 of the present invention degrades isopropanol, ethanal, dipropyl disulfide, diethyl disulfide and propanethiol and its growth.
Figure 2B:
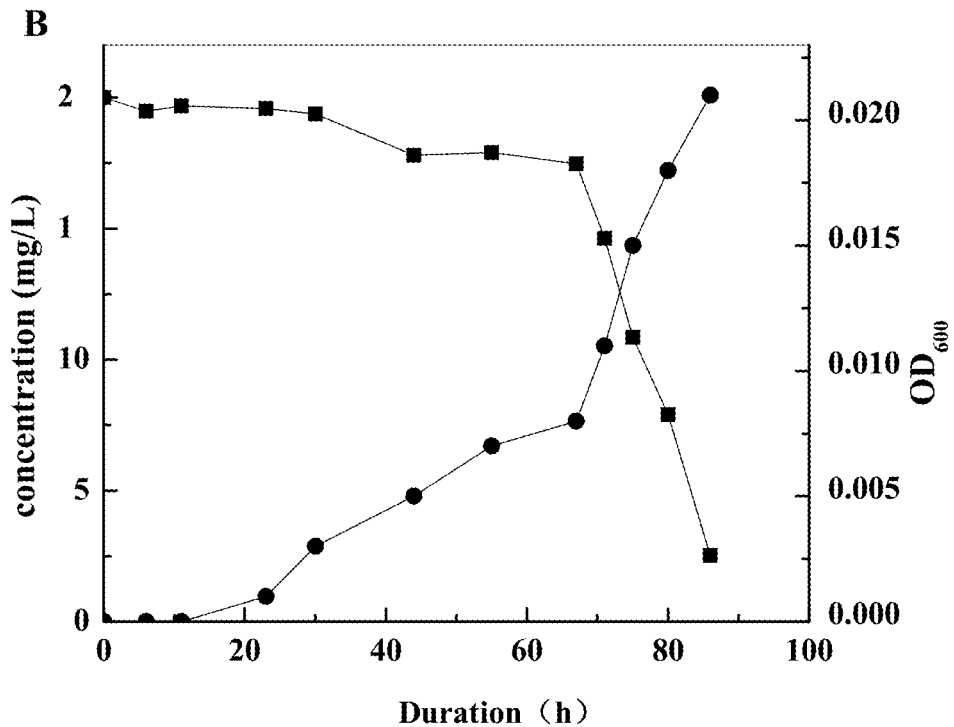
Figure 2C:
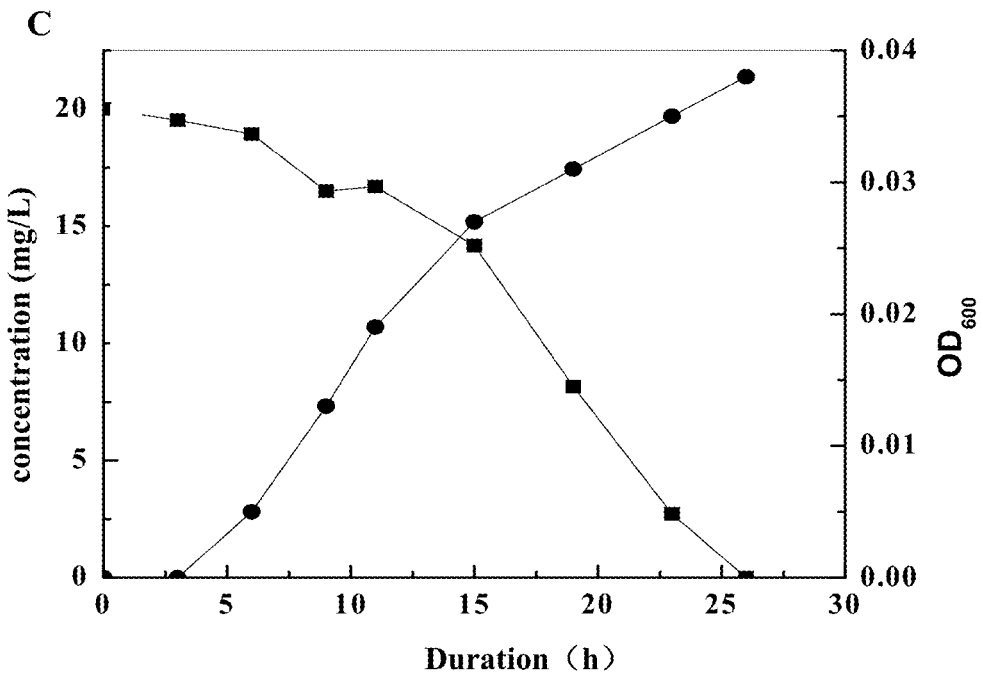
Figure 2D:
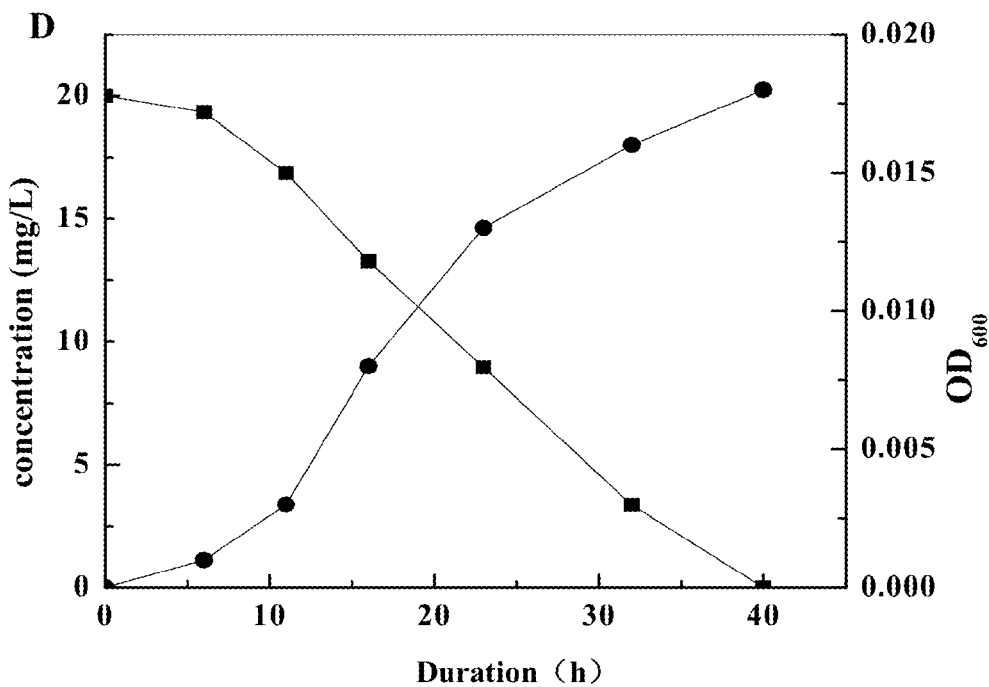
Figure 2E:
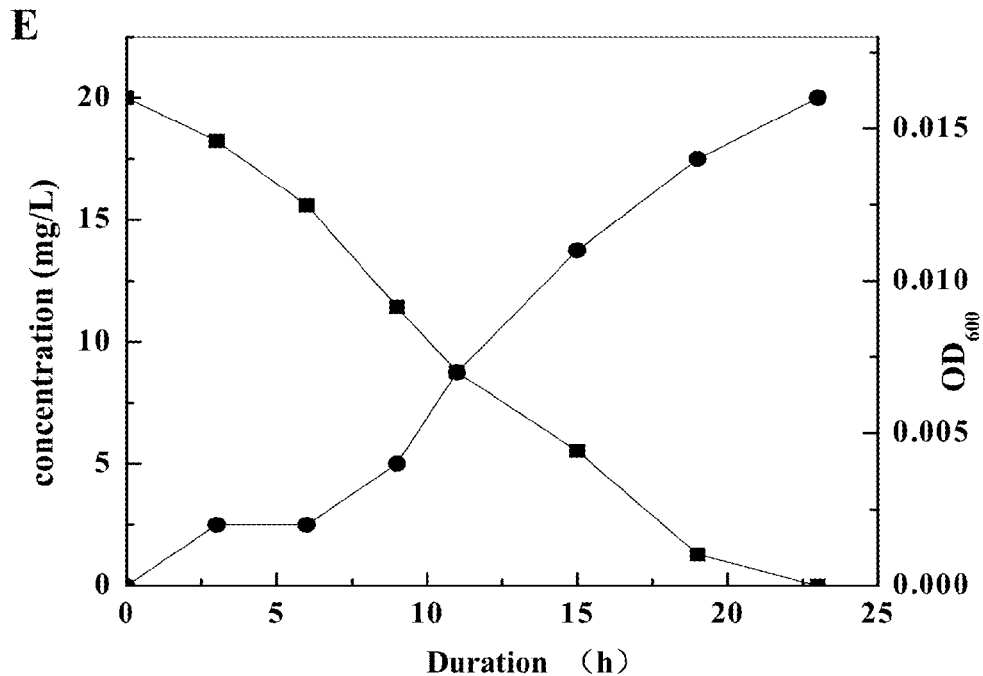
Figure 3A:
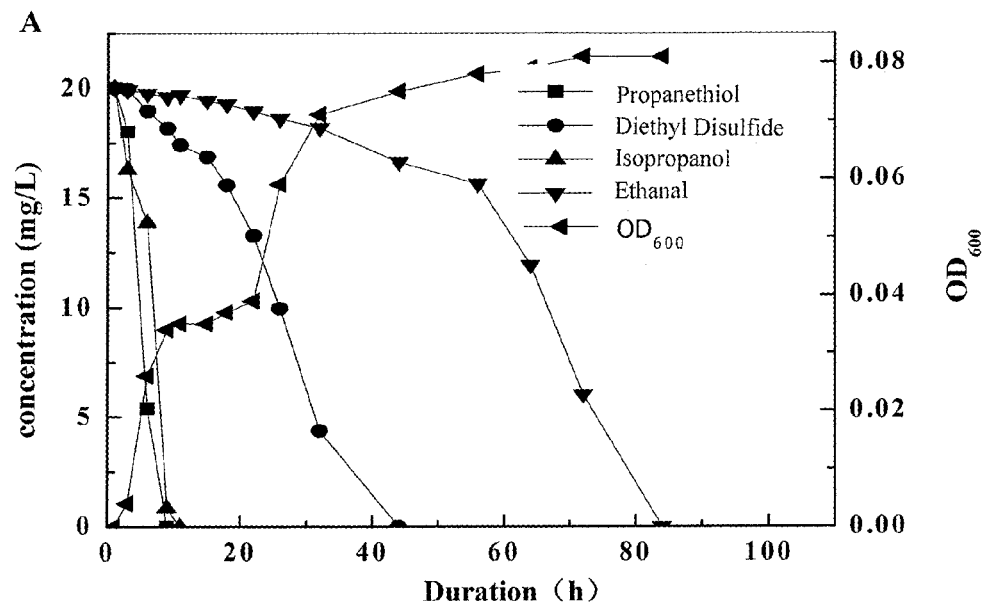
FIG. 3A, FIG. 3B, FIG. 3C and FIG. 3D show how *pseudomonas putida* S-1 of the present invention degrades isopropanol, ethanal, diethyl disulfide and propanethiol in different preliminary culture modes and its growth.
Figure 3B:
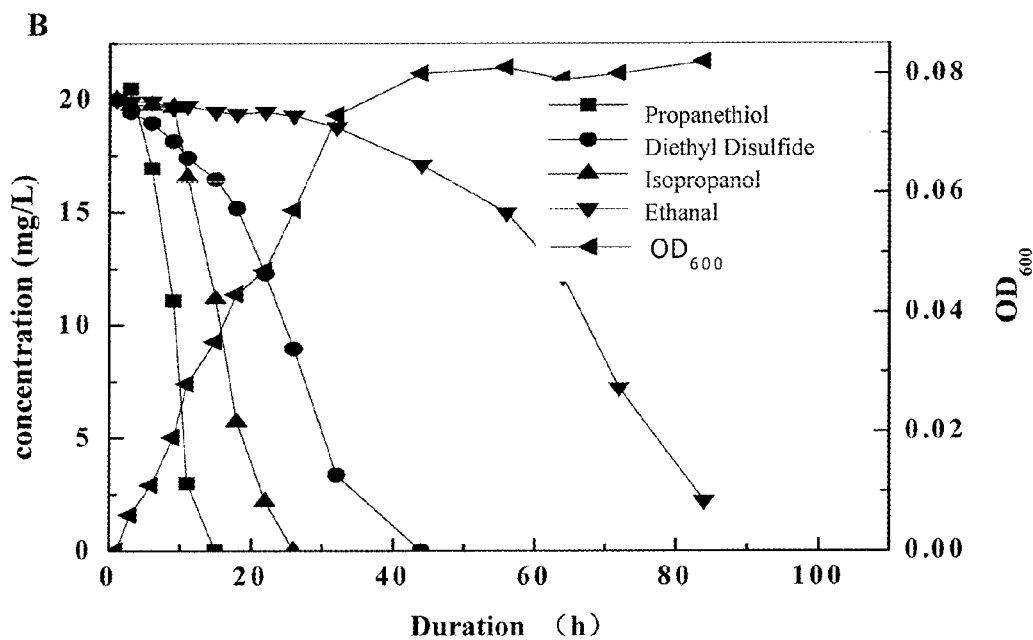
Figure 3C:
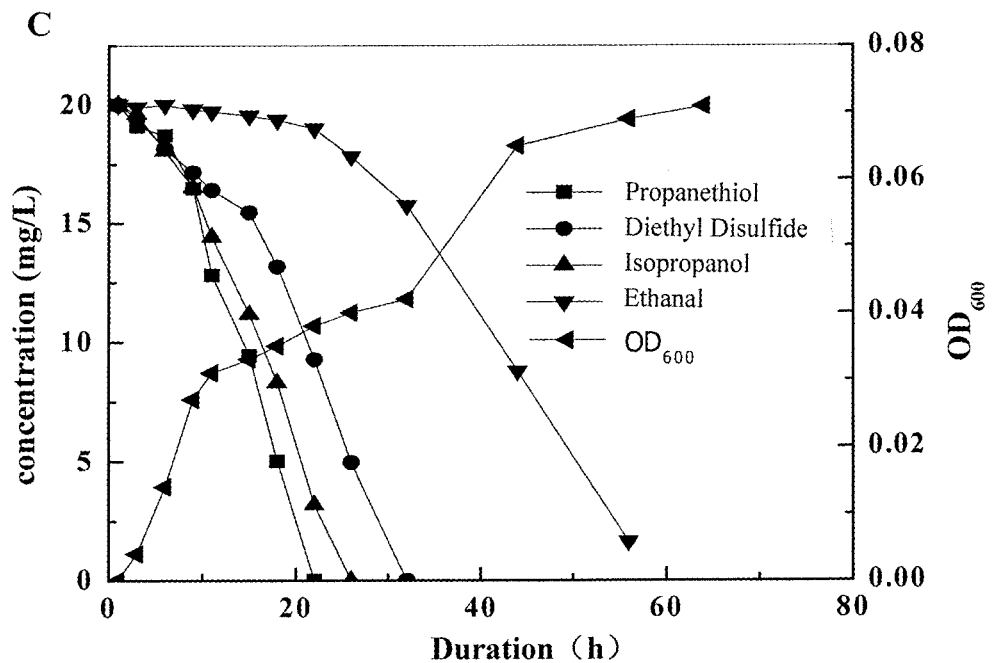
Figure 3D:
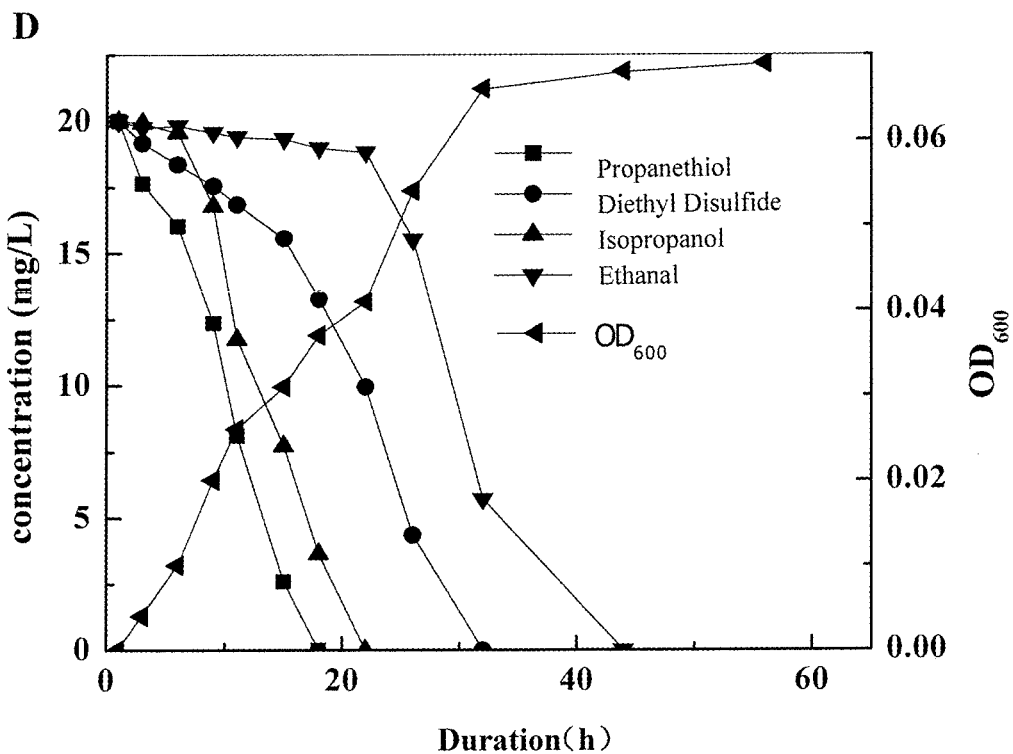

As shown in FIG. 1, the strain cell is rod-shaped with size up to (0.4-0.7)μm×(1.4-1.7)μm, with flagella but no gemmae; the small round bacteria colony is white with plump profile, smooth, wet and easy to be picked; the lawn grows along the streak, aerobic, with positive oxydase reaction; positive arginine hydrolase and catalase, and negative in indole reaction, M.R. reaction, V.P. reaction and gram staining.

The strain was transferred into the hole on the BIOLOG® micro plate for culture in the incubator under the temperature of 30° C. for 24 h; test results were as shown in Table 1:

TABLE 1

| Biochemical Testing Results | | | | | |
|---|---|---|---|---|---|
| Biochemical items | Results | Biochemical items | Results | Biochemical items | Results |
| Negative control | − | Inosine | − | D-glucuronic acid | − |
| Dextrin | − | Sodium lactate | + | glucuronamide | B |
| D-Malt | − | Fusidic acid | − | Galactaricacid; | + |
| D-Mycose | − | D-Serine | B | mucic acid | |
| D-Cellobiose | − | D-Sorbitol | − | Quininic acid | + |
| Gentiobiose | − | D-Mannitol | B | Saccharic acid | + |
| Sucrose | − | D-Arabitol | − | Vancomycin | + |

TABLE 1-continued

Biochemical Testing Results

| Biochemical items | Results | Biochemical items | Results | Biochemical items | Results |
|---|---|---|---|---|---|
| D-turanose | − | Inositol | − | Tetrazolium violet | + |
| Stachyose | − | Glycerol | B | Tetrazolium blue | + |
| Positive control pH 6 | + | D-Glucose-6-orthophosphoric acid | − | p-oxhydryl-phenylacetic acid | − |
| pH 5 | + | D-frucose-6-orthophosphoric acid | B | Methyl pyruvate | B |
| Raffinose | − | | | D-methyl lactate | B |
| α-D-lactin | − | D-Asparagic acid | − | L-lactic acid | + |
| Melibiose | − | D-serine | − | Citric acid | + |
| β-formyl-D-glucoside | − | Troleandomycin Rifamycin, SV | + + | α-ketone-glutaric acid | + |
| D-salicin | − | Minocycline | − | D-malic acid | − |
| N-acetyl-D-Glucosamine | B | Gelatin Glycyl-L-proline | − − | Lmalic acid Br-succinic acid | + B |
| N-acetyl--D-mannosamine | − | L-alanine L-arginine | + B | Nalidixic acid Lithium chloride | − − |
| N-acetyl-D-galactosamine | − | L-Asparagic acid L-Glutamic acid | B + | Potassium tellurate Tween 40 | − − |
| N-acetylneuraminic acid | − | L-histamine L-pyroglutamic acid | + B | γ-azyl-butyrate α-oxhydryl-butyrate | B − |
| 1% NaCl | + | L-serine | B | β-oxhydryl-D,L-butyrate | B |
| 4% NaCl | B | Lincomycin, jiemycin | + | | |
| 8% NaCl | − | | | | |
| α-D-glucose | + | Guanidine hydrochloride | B | α-acetone-butyrate Acetacetic acid | − − |
| D-mannose | + | | | | |
| D-fructose | B | Tetradecyl sodium sulfate | + | Propionic acid Acetic acid | − B |
| D-galactose | + | | | | |
| 3-Phenyl benzamide | − | Pectin D-Galacturonic acid | − − | Formic acid Aztreonam | − B |
| D-fructose | B | L-galacturonic acid | − | Sodium butyrate | − |
| L-fructose | B | D-gluconic acid | + | Sodium bromate | B |
| L-rhamnose | − | | | | |

Note:
"+"—positive; "−"—negative; "B"—boundary value.

A genome extraction kit was used to extract the complete genome of the strain for PCR amplification of strain DNA, and obtain approximate 1500 bp amplification product of 16S rRNA; the amplification primer is the universal primer F8 (5'-AGAGTTTGATCCTGGCTCAG-3') and R1541 (5'-AGAAAGGAGGTGATCCAGCC-3') in consensus sequence of bacteria as shown in SEQ ID NO.1. According to homologous comparison with gene sequence in GenBank, similarity between the strain and *Pseudomonas putida* of type strain—PSEIAM19 (*Pseudomonas putida* PSEIAM19, GenBank: D84020.1) is up to 98%.

As indicated by Biolog system and verification results of 16S rRNA, the strain obtained through separation is *Pseudomonas putida*, named as *Pseudomonas putida* S-1 (hereinafter referred to as Strain S-1); it was preserved at China Center for Type Culture Collection of Wuhan University on Sep. 25, 2013 with the deposit number of CCTCC NO: M2013444. GenBank: KF640247.1

Embodiment 3

Degrading of Isopropanol, Ethanal, Dipropyl Disulfide, Diethyl Disulfide and Propanethiol with Strain S-1

Taking isopropanol for instance, transplant thallus was taken from the solid culture medium to 50 mL fresh liquid inorganic salt culture medium, and the initial concentration of thallus (based on $OD_{600}$) was controlled at 0.01; 20 mg/L isopropanol was added into it for culture in the table concentrator with temperature and revolution up to 30° C. and 160 r/min respectively; 3 parallel samples and 1 blank contrast (similarly hereinafter) were designed during the test. Samplings were obtained at the specified interval to test variation of the thallus OD600 and degrading speed of isopropanol. Degradation of isopropanol, ethanal, dipropyl disulfide, diethyl disulfide and propanethiol were tested by reference to the aforesaid testing method.

As shown in FIG. 2, 20 mg/L dipropyl disulfide and propanethiol can be fully degraded within 25 hours; whereas concentration of thallus will witness a gradual increase as the time passes; strain S-1 can degrade over 90% the 20 mg/L isopropanol and diethyl disulfide within 35 hours; however, it will take a relatively long lag phase for S-1 to degrade ethanal; 20 mg/L ethanal can be fully degraded once the strain enters the logarithmic phase. As indicated by this embodiment, *Pseudomonas putida* S-1 can take isopropanol, ethanal, dipropyl disulfide, diethyl disulfide and propanethiol as the sole carbon source and energy for growth, with stable and efficient degrading performance.

Specific growth rate of strain S-1 for degrading 20 mg/L isopropanol, ethanal, dipropyl disulfide, diethyl disulfide and propanethiol is listed in Table 2.

TABLE 2

Specific Growth Rate of Strain S-1

| Different Substrates | Isopropanol | Dipropyl Disulfide | Aldehyde | Diethyl Disulfide | Propanethiol |
|---|---|---|---|---|---|
| Specific growth rate $(h^{-1})$ | 0.026 | 0.021 | 0.021 | 0.038 | 0.021 |

Embodiment 4

Degrading of Mixture of Isopropanol, Ethanal, Diethyl Disulfide and Propanethiol with Strain S-1

The preparation of seed liquid: A) using eutrophia medium to culture strain S-1 to obtain the seed liquid a; constituents of eutrophia medium are stated as follows: 1-5 g/L peptone, 0.2-1 g/L yeast powder and 10.5-2.5 g/L NaCl;

B) adding 200 mg/L Propanethiol into an inorganic salt culture medium to culture strain S-1 to obtained seed liquid b;

C) using citric acid culture medium to culture strain S-1 to obtain seed liquid c; constituents of culture medium are stated as follows: 0.5-2 g/L citric acid, 1-4 g/L $NH_4Cl$, 0.1-0.3 g/L $MgCl_2$ and 0.005-0.05 g/L $FeCl_2$.

D) using the inorganic salt culture medium added with 0.5-2 g/L yeast powder to culture strain S-1 to obtain seed liquid d.

The seed liquid was transferred to a fresh 50 mL inorganic salt culture medium, and the concentration ($OD_{600}$) of the initial thallus was controlled at 0.01; 20 mg/L isopropanol, ethanal, diethyl disulphide and propanethiol were added into it for culture in the table concentrator with temperature and revolution up to 30° C. and 160 r/min respectively; samplings were taken at the specified interval, and the variation of the thallus $OD_{600}$ and the substrate concentration were checked; results are as shown in FIG. 3.

Viewing from FIG. 3, it can be seen that substrate degrading speed of different seed liquids is varied. Difference in seed liquid culture mode only has slight impact on degrading of diethyl disulfide; the transferred seed liquid (3A) can significantly shorten the time for degrading isopropanol and propanethiol; with regard to ethanal, lag phase of seed liquid (3C) and (3D) is shorter than that of seed liquid (3A) and (3B), and faster in degrading speed; strain S-1 degrades various substances in the following sequence: propanethiol, isopropanol, diethyl disulfide and ethanal.

Embodiment 5

Impact of pH, Temperature and Salinity on Degrading Performance of Strain S-1

Taking propanethiol as an instance, impact of different pH values (4.0, 5.0, 6.0, 7.0, 8.0, 9.0 and 10.0), temperatures (15° C., 20° C., 25° C., 30° C. and 37° C.) and salinity (0%, 0.4%, 0.85%, 1.5% and 3.0%) on strain S-1 is examined. Initial concentration of propanethiol and thallus is 50 mg/L and 0.01 (based on $OD_{600}$), respectively. The samples were put into 160 r/min thermostatic incubator for shaking culture, and samplings were taken at the specified interval to check concentration of propanethiol contained in the reaction liquid; results are as shown in FIG. 4.

Figure 4A:
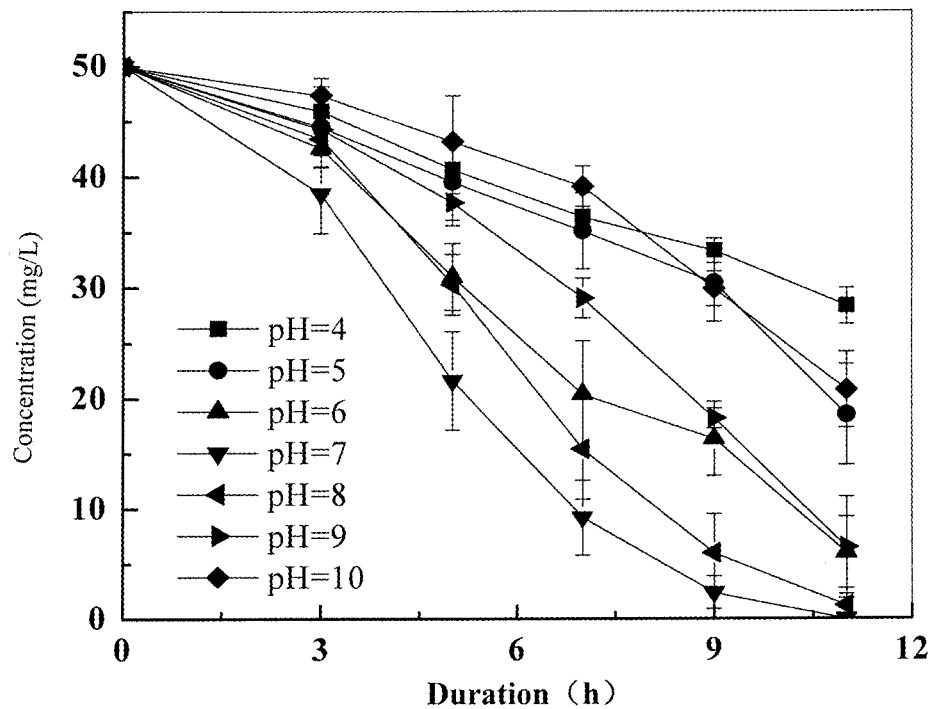
FIG. 4A, FIG. 4B and FIG. 4C show the impact of pH, temperature and salinity on degrading of propanethiol.
Figure 4B:
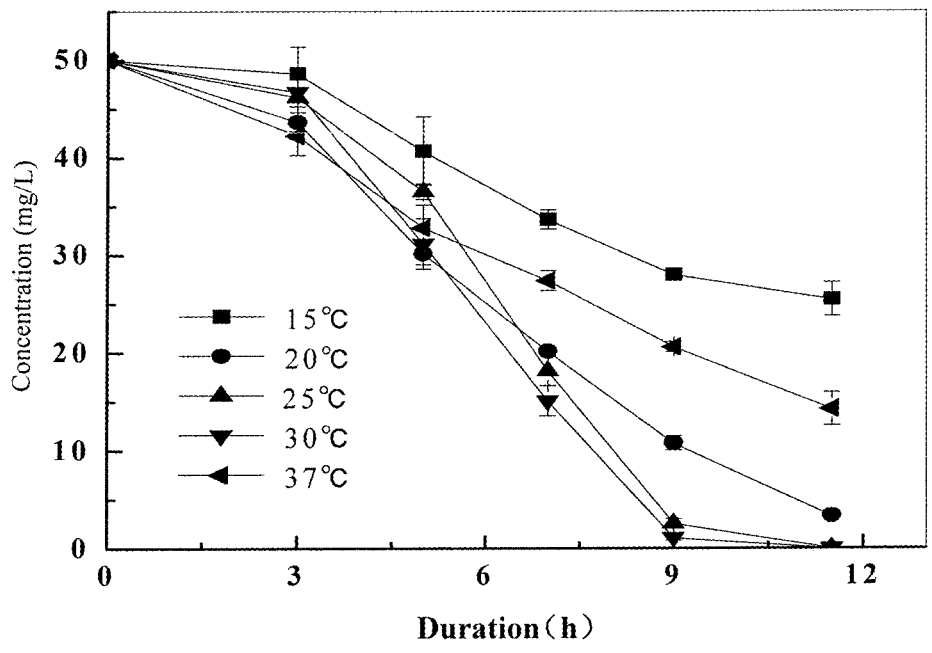
Figure 4C:
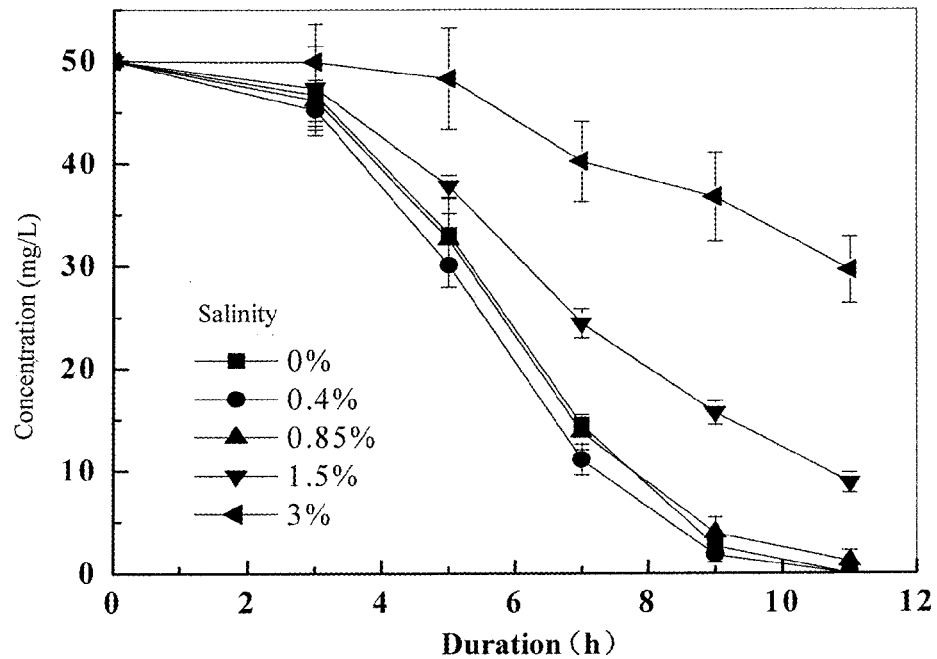

Viewing from FIG. 4A, it can be seen that the *pseudomonas putida* S-1 has certain degrading performance under the pH of 4.0-10.0; once pH is increased from 4.0 to 10.0, thallus degrading performance will witness an increase and decrease in turn; pH appropriate for growth of S-1 is 7.0. Viewing from FIG. 4B, it can be seen that the thallus degrading performance will witness an increase and decrease in turn when the temperature is increased from 15° C. to 37° C.; the temperature appropriate for growth of S-1 is 25-30° C. As indicated by FIG. 4C, lower salinity is favorable for growth of strain; whereas higher salinity may restrict the strain degrading performance.

Embodiment 6

Fermentation of Liquid Strain S-1

A) Stirred Fermentation

A 6 L fermentation medium was added into the 10 L fermentor; its constituents are stated as follows: 0.1-1% malt extract, 0.5-2% peptone, 0.5-2% bean cake powder, 1-5% corn meal and 0.5-1% MgCl2; sterilization was conducted under the temperature of 121° C. for 20 min.

The fermentor was sterilized under the temperature of 121° C. for 20 min before transplantation and feeding; the medium was cooled down to the room temperature before transplantation; the transplantation volume was controlled at 1%-5%, the medium temperature at 25-30° C., pH at 6-7, the stirring revolution at 400 r/min and the ventilation capacity at 1:1.2 v.v.m (unit air content of the same volume as contained in the medium per minute) respectively; fermentation was conducted for 10 hours before adding appropriate amount of carbon and nitrogen source for further fermentation for 15-20 hours; fermentation was stopped once the thallus concentration was up to 2.6 ($OD_{600}$); cell growth concentration is as shown in Table 3. The fermentation broth was filled into containers under aseptic condition for preservation under low temperature.

TABLE 3

Growth of Bacteria Subjecting to Stirred Fermentation

| | Duration (hours) | | | | |
|---|---|---|---|---|---|
| | 0 | 5 | 10 | 15 | 20 |
| $OD_{600}$ | 0.010 | 0.494 | 1.465 | 1.962 | 2.442 |

B) Airlift Fermentation

An internal-loop airlift fermentator is a fermentator of non-mechanical agitation that makes use of rising air to realize circulation and turbulence for gas-liquid mixing. The airlift fermentator used has an effective volume of 10 L, whose main body is in cylinder shape; it is made of plexiglass with cylinder height, diameter and floor area up to 50 cm, 18 cm and 0.25 $m^2$ respectively. Constituents of fermentation medium, transplantation volume, sterilization conditions, temperature, pH and ventilation were the same as that of stirred fermentator. Growth of cell during fermentation is as shown in Table 4.

TABLE 4

Growth of Bacteria under Airlift Fermentation

| | Duration (hours) | | | | |
|---|---|---|---|---|---|
| | 0 | 5 | 10 | 15 | 20 |
| $OD_{600}$ | 0.010 | 0.611 | 1.851 | 2.447 | 2.795 |

Embodiment 7

Semi-Solid Fermentation of Strain S-1

The constituents of semi-solid fermentation medium were stated as follows: 20 g citric acid, 10 g starch, 10 g peptone, 1 g K2HPO4, 0.5 g MgCl2, 2 g agar and 1 L water. A 30 mL medium was added into the conical flask for sterilization under the temperature of 121° C. for 20 min. After that, 5% activated strain S-1 was transplanted to each flask for semi-solid fermentation under the temperature of 25-30° C.; the fermentation was stopped once the biomass was over $10^{12}$/g.

An appropriate amount of fermentation substance was added into an inorganic medium, and an initial $OD_{600}$ controlled at 0.01 to examine degradation of 20 mg/L isopropanol, ethanal, dipropyl disulfide, diethyl disulphide and propanethiol. 10-hour degrading rate of propanethiol was over 80%; whereas 25-hour degrading rate of isopropanol and dipropyl disulfide was up to 100% and 78% respectively; 45-hour degrading of diethyl disulphide was 93%; whereas 75-hour degrading rate of ethanal was 89%.

Embodiment 8

Solid Fermentation of Strain S-1

The constituents of the medium for solid fermentation were stated as follows: 10 g turf, 10 g wheat bran, 5 g beef extract, 4.5 g peptone, 0.2 g citric acid, 0.1 g MgCl2, 0.1 g FeCl2 and 0.1 g CaCl2. A 30 g fermentation medium and 25 mL tap water were added into 250 mL conical flask for sterilization under the temperature of 121° C. for 20 min. After that, 5% activated strain S-1 was further added into each flask for solid fermentation under the temperature of 25-30° C.; the fermentation substance was dried under the room temperature once the biomass was over $10^{12}$/g.

Impact of preservation duration of solid fermentation substance on degradation was examined. The solid fermentation substance of different preservation duration was added into an inorganic salt medium containing 20 mg/L isopropanol for 160 r/min culture under the temperature of 30° C.; 30-hour degrading rate of isopropanol is as shown in Table 5. Viewing from the table, it can be seen that solid fermentation substance features in relatively stable activity; the removal rate was still over 85% despite of the fact it has decreased after 25 days.

TABLE 5

Degrading Effect Following Preservation for Different Duration

| | Preservation duration (day) | | | | | | | |
|---|---|---|---|---|---|---|---|---|
| 1 | 4 | 7 | 10 | 13 | 16 | 19 | 22 | 25 |
| Removal rate (%) 92.7% | 93.2% | 91.3% | 92.6% | 90.8% | 91.3% | 89.7% | 88.5% | 86.2% |

Embodiment 9

Preparation of Solid Microbial Inoculum of Strain S-1

Strain S-1 obtained through the solid fermentation in Embodiment 8 was selected as solid microbial inoculum A.

The preparation method of solid microbial inoculums B was as follows: a microbial inoculums carrier comprises an activated carbon powder, sawdust, a dry soil and diatomaceous earth with weight percentage up to 65%, 20%, 10% and 5%, respectively; a 50 g carrier was added into each 500 mL conical flask following uniform mixing. A 20 g liquid or semi-solid fermented strain S-1 was added into the aforesaid carrier as prepared for uniform mixing; after that, proceed with thermostatic culture under the temperature of 30° C. for 1 hour before adding 3-10 g agar (added at the temperature of 50° C.) for wrapping to obtain solid S-1 microbial inoculums.

Embodiment 10

Preservation Stability of Microbial Inoculum

Figure 5:
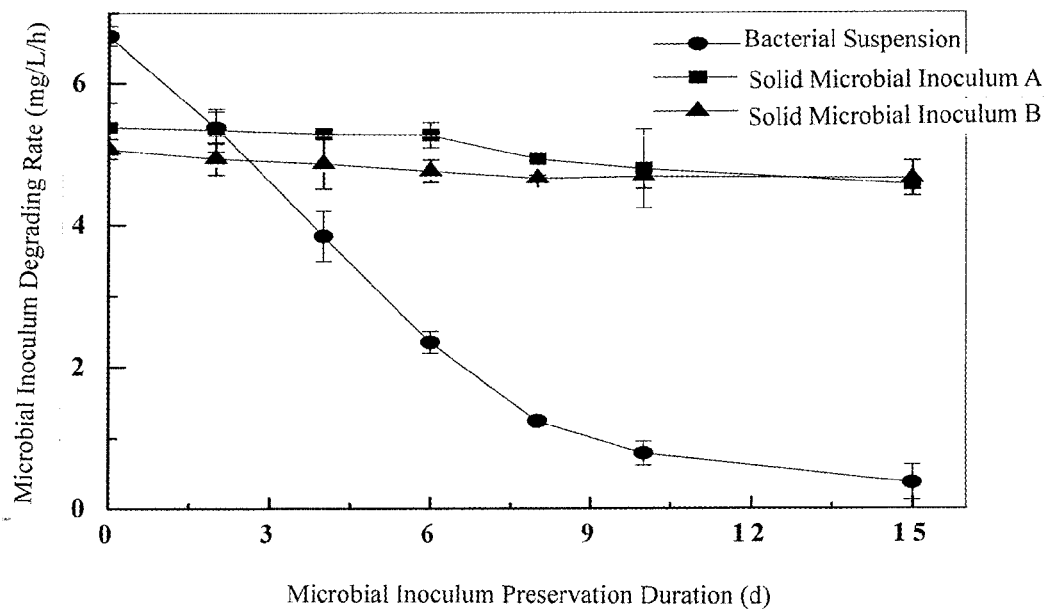
FIG. 5 shows the degrading activity of different inoculums after preservation at room temperature.

The microbial inoculums A and B obtained as well as the bacterial suspension were placed under the room temperature (20° C.) for different duration to check their stability in degrading isopropanol; results are as shown in FIG. 5. Solid S-1 microbial inoculums has satisfactory activity within 10 days; as time extends, solid microbial inoculums can exhibit its stable advantage in maintaining relatively higher degrading activity within a longer period of time. After preservation for 15 days, degrading activity of solid microbial inoculums A and B is obviously higher than that of bacterial suspension. Solid microbial inoculums can maintain its degrading rate over 70% after preservation under the room temperature for 2 months. This indicates that solid microbial inoculum has higher stability, which is more favorable for engineering application.

Embodiment 11

Substrate Tolerance of Microbial Inoculum

Bacteria liquid, semi-solid microbial inoculum, solid microbial inoculums A and B containing *P. putida* S-1 were added into an inorganic salt medium containing 2000 mg/L isopropanol or propanethiol to degrade pollutants. The removal rates of isopropanol were up to 40%, 56%, 62% and 64%, respectively, after degrading for 5 days; whereas those of propanethiol were up to 52%, 71%, 83% and 89%, respectively. This indicates that *P. putida* S-1 has perfect substrate tolerance that is higher than that of reported strain as degraded with isopropanol or propanethiol.

Embodiment 12

Purification of Mixed Exhaust Gas of Isopropanol, Ethanal, Diethyl Disulfide and Propanethiol with Strain S-1

Figure 6:
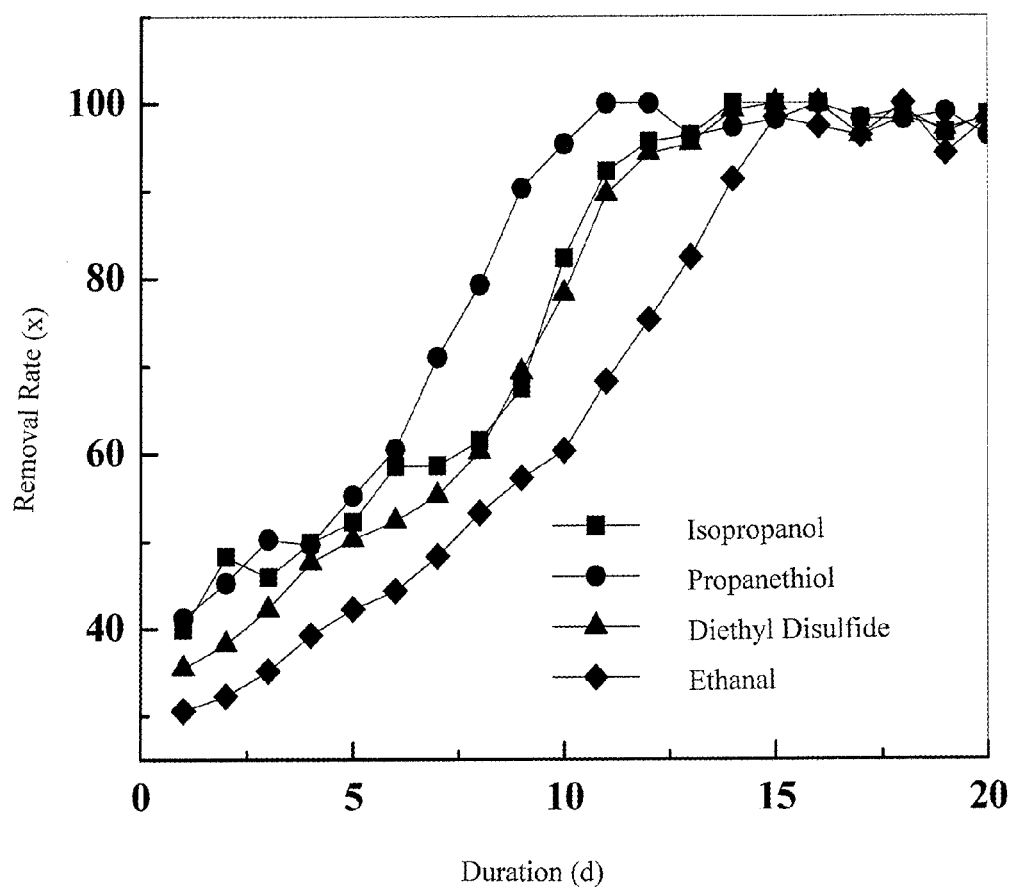
FIG. 6 shows how the biotrickling filter purifies the exhausted gas mixed with isopropanol, ethanal, diethyl disulfide and propanethiol

The S-1 solid microbial inoculum B was added in Embodiment 9 into the biotrickling filter for continuous treatment of 100 mg/m³ mixed exhaust gas of isopropanol, ethanal, diethyl disulfide and propanethiol. As shown in FIG. 6, following film-formation actuation for 20 days, the removal rates of various substances were maintained over 90% within the duration of 40 seconds. After that, the system can maintain its stable operation.

The invention claimed is:

1. A *Pseudomonas putida* strain characterized in that it is named as *Pseudomonas putida* S-1 and preserved on Sep. 25, 2013 with the number of CCTCC NO: M2013444.

2. The *Pseudomonas putida* strain as claimed in claim 1 wherein the *Pseudomonas putida* strain's cell is rod-shaped, with flagella but no gemmae; a small round bacteria colony is white with plump profile, smooth, wet and easy to be picked; the lawn grows along the streak, aerobic, with positive oxydase reaction; positive arginine hydrolase and catalase, and negative in indole reaction, methyl red reaction, Voges-Proskauer reaction and gram staining.

3. A microbial inoculum containing the *Pseudomonas putida* strain as claimed in claim 1.

4. The microbial inoculum as claimed in claim 3 characterized in that it is in solid form.

5. The microbial inoculum as claimed in claim 4 characterized in that it is mixed by a liquid bacteria and a carrier; the carrier comprises an activated carbon powder, sawdust, dry soil and diatomaceous earth.

6. The microbial inoculum as claimed in claim 4 characterized in that the solid microbial inoculum is directly obtained through solid-state fermentation.

7. The microbial inoculum as claimed in claim 3 characterized in that it belongs to semi-solid microbial inoculum.

8. The microbial inoculum as claimed in claim 7 characterized in that the semi-solid microbial inoculum is obtained through semi-solid fermentation whose culture medium for semi-solid fermentation takes agar as the solid.

9. A method of decomposition of a volatile organic compound comprising the step of:
contacting the volatile organic compound with a *Pseudomonas putida* strain and a microbial inoculum containing the *Pseudomonas putida* strain,
wherein the *Pseudomonas putida* strain is named as *Pseudomonas putida* S-1 and preserved on Sep. 25, 2013 with the number of CCTCC NO: M2013444; and
wherein the volatile organic compound comprises isopropanol, ethanal, diethyl disulfide and propanethiol.

10. The method as claimed in claim 9 characterized in that the decomposition is conducted at a pH value of 4.0~10.0, a temperature of 15° C.~370° C. and salinity of 0%~3%.

11. A method for treating an exhaust gas containing a volatile organic compound comprising the following steps:
(1) transplanting *Pseudomonas putida* S-1 or a microbial inoculum containing such strain to a bioreactor;
(2) passing the exhaust gas through the bioreactor;
wherein the *Pseudomonas putida* strain is named as *Pseudomonas putida* S-1 and preserved on Sep. 25, 2013 with the number of CCTCC NO: M2013444; and
wherein the volatile organic compound comprises isopropanol, ethanal, diethyl disulfide and propanethiol.

12. The method as claimed in claim 11 characterized in that the bioreactor is used at a pH value of 6.0~8.0, a temperature of 25° C.~30° C. and salinity of 0%~1.5%.

13. The method as claimed in claim 11 characterized in that the bioreactor is a stirred bioreactor, an airlift bioreactor or a biotrickling filter.

14. The method as claimed in claim 11 characterized in that the bioreactor is a biotrickling filter.

15. The method as claimed in claim 9 wherein the *Pseudomonas putida* strain's cell is rod-shaped, with flagella but no gemmae; a small round bacteria colony is white with plump profile, smooth, wet and easy to be picked; the lawn grows along the streak, aerobic, with positive oxydase reaction; positive arginine hydrolase and catalase, and negative in indole reaction, methyl red reaction, Voges-Proskauer reaction and gram staining.

16. The method as claimed in claim 10 wherein the *Pseudomonas putida* strain's cell is rod-shaped, with flagella but no gemmae; a small round bacteria colony is white with plump profile, smooth, wet and easy to be picked; the lawn grows along the streak, aerobic, with positive oxydase reaction; positive arginine hydrolase and catalase, and negative in indole reaction, methyl red reaction, Voges-Proskauer reaction and gram staining.

\* \* \* \* \*